(12) United States Patent
Hagen et al.

(10) Patent No.: US 7,253,321 B2
(45) Date of Patent: Aug. 7, 2007

(54) PROCESS FOR THE PREPARATION OF POLYAMINES OF THE DIPHENYLMETHANE SERIES AT A LOW DEGREE OF PROTONATION

(75) Inventors: Torsten Hagen, Essen (DE); Daniel Koch, Duisburg (DE); Hans-Georg Pirkl, Leverkusen (DE); Fritz Pohl, Brunsbüttel (DE); Stefan Wershofen, Mönchengladbach (DE); Rudolf Uchdorf, Krefeld (DE); Richard Adamson, Leichlingen (DE)

(73) Assignee: Bayer MaterialScience AG, Leverkusen (DE)

( * ) Notice: Subject to any disclaimer, the term of this patent is extended or adjusted under 35 U.S.C. 154(b) by 238 days.

(21) Appl. No.: 11/170,624

(22) Filed: Jun. 29, 2005

(65) Prior Publication Data
US 2006/0287555 A1    Dec. 21, 2006

(30) Foreign Application Priority Data
Jul. 5, 2004  (DE) ............ 10 2004 032 416

(51) Int. Cl.
*C07C 209/78*  (2006.01)
(52) U.S. Cl. .............. 564/409; 564/326; 560/347; 560/358; 560/359
(58) Field of Classification Search ............ 564/326
See application file for complete search history.

(56) References Cited

U.S. PATENT DOCUMENTS

| 3,517,062 | A |   | 6/1970 | Powers .............. 260/570 |
| 4,259,526 | A | * | 3/1981 | Dunlap et al. ........ 564/331 |
| 6,433,219 | B1 |  | 8/2002 | Ströfer et al. ........ 560/347 |
| 6,639,102 | B2 |  | 10/2003 | Hagen et al. ......... 560/347 |
| 6,831,192 | B2 |  | 12/2004 | Ströfer et al. ........ 560/347 |
| 2004/0002579 | A1 |  | 1/2004 | Hagen et al. ......... 528/266 |
| 2005/0014975 | A1 |  | 1/2005 | Stofer et al. ......... 564/330 |
| 2005/0222291 | A1 | * | 10/2005 | Pirkl et al. ............ 521/159 |
| 2005/0240054 | A1 | * | 10/2005 | Liman et al. .......... 560/347 |

FOREIGN PATENT DOCUMENTS

DE       1 011 337        6/1957
DE    198 04 918 A1       8/1999

* cited by examiner

*Primary Examiner*—Brian Davis
(74) *Attorney, Agent, or Firm*—Joseph C. Gil; Lyndanne M. Whalen; N. Denise Brown

(57) ABSTRACT

The invention provides a process for the preparation of polyamines of the diphenylmethane series. This process comprises
  a) reacting aniline and formaldehyde in a molar ratio of 1.5:1 to 6:1, in the presence of an acid catalyst at temperatures of 20° C. to 100° C., in which the water content in the acid reaction mixture is <20 wt. % and a degree of protonation of <15% is established, and
  b) increasing the temperature of the reaction to a temperature of 110° C. to 250° C. when the ratio of the weight contents of p-aminobenzylaniline to 4,4'-MDA in the reaction mixture falls below a value of 1.00.

9 Claims, No Drawings

PROCESS FOR THE PREPARATION OF POLYAMINES OF THE DIPHENYLMETHANE SERIES AT A LOW DEGREE OF PROTONATION

BACKGROUND OF THE INVENTION

The present invention relates to a process for the preparation of polyamines of the diphenylmethane series.

Polyamines of the diphenylmethane series are understood as being compounds and compound mixtures which correspond to the following general formula:

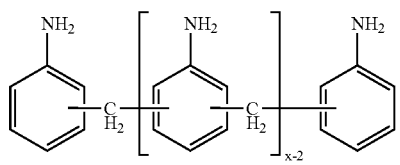

wherein:

x represents a number from 2 to n, and n represents a natural number >2.

The continuous, discontinuous or semi-continuous preparation of polyamines of the diphenylmethane series, also called MDA in the following, is described in numerous patents and publications (see e.g. H. J. Twitchett, Chem. Soc. Rev. 3(2), 209 (1974), M. V. Moore in: Kirk-Othmer Encycl. Chem. Technol., 3rd ed., New York, 2, 338-348 (1978)). The preparation is conventionally carried out by the reaction of aniline and formaldehyde, in the presence of acid catalysts. HCl is conventionally employed as the acid catalyst. According to the prior art, the acid catalyst is neutralized, and therefore used up, by addition of a base at the end of the process and before the final working up steps (such as, for example, removal of excess aniline by distillation).

Generally, it is known that acid condensation of aromatic amines and formaldehyde to yield polyamines of the diphenylmethane series proceeds in several reaction steps. These are explained, by way of example, in the following equation:

Condensation:

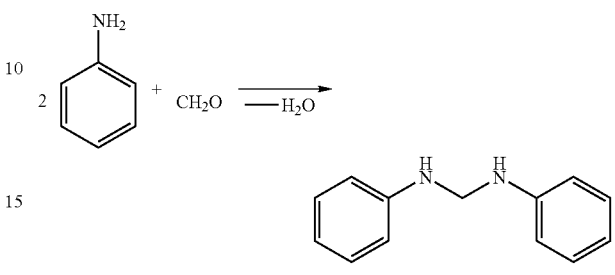

1st rearrangement:

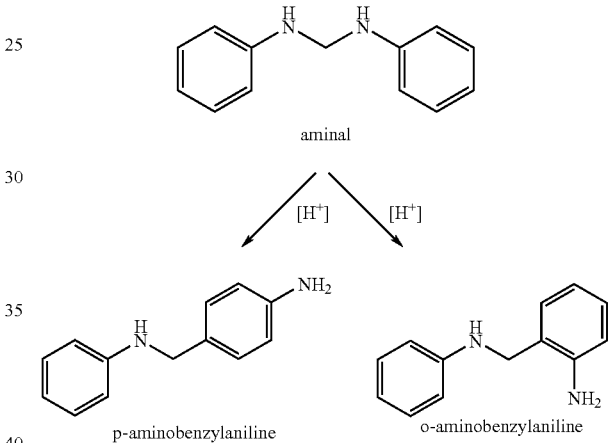

2nd rearrangement:

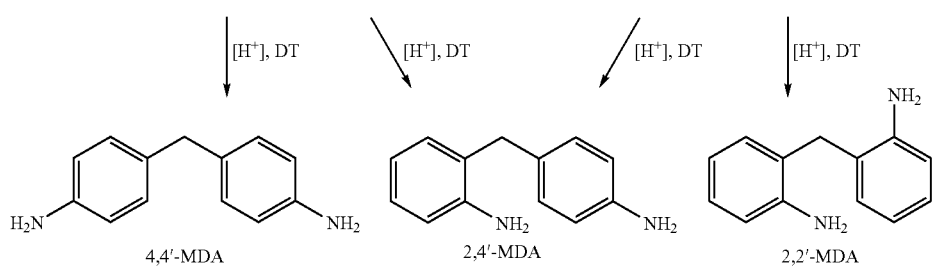

In the absence of an acid catalyst, formaldehyde first undergoes condensation with aniline to yield so-called aminal and water. The rearrangement that results in MDA takes place under acid catalysis in a first step to yield para- and ortho-aminobenzylaniline. The aminobenzylanilines then rearrange in a second step to give MDA. The main products of the acid-catalysed reaction of aniline and formaldehyde are the diamine 4,4'-MDA, its position isomers 2,4'-MDA and 2,2'-MDA, and higher homologous polyamines of the diphenylmethane series.-

In the presence of an acid catalyst, the aminobenzylanilines are formed directly from aniline and formaldehyde. These then react further to yield the MDA isomers having two rings and MDA homologues having more than two rings.

Polyisocyanates of the diphenylmethane series, called MDI herein, are prepared by phosgenation of the corresponding polyamines. The polyisocyanates of the diphenylmethane series prepared in this way contain here the various isocyanate isomers and higher homologues thereof in the same relative amounts as the polyamines from which they have been prepared.

A controlling parameter for influencing the distribution of isomers in the acid-catalysed reaction of aniline and formaldehyde is, in addition to the molar ratio of aniline and formaldehyde, the amount of acid catalyst employed in the process. In this connection, the degree of protonation of monoproton acids, such as HCl, is the molar ratio of the acid catalyst employed and the molar amount of amine functions present in the reaction mixture. In order to be able to prepare MDA with the desired distribution of isomers, sometimes considerable amounts of acid catalyst (which corresponds to a high degree of protonation), and correspondingly considerable amounts of base for the neutralization of the acid catalyst, must therefore be employed.

Thus, DE-A-1 643 449 describes the preparation of MDA having a high content of 4,4'-MDA by reaction of aniline which has been reacted with acid before being reacted with formaldehyde, such that the degree of protonation is at least 25%, preferably at least 50%, and more preferably 75 to 100%. In this context, it is necessary to employ the acid catalyst in an amount such that the reaction is carried out in a uniform phase. Both the water of reaction and the water originating from the starting substances remain in the reaction mixture.

DE-A-10 111 337 describes the preparation of MDA at a degree of protonation of <20%, however, MDA having an increased content of the 2,4' isomer is obtained according to the invention. This process also discloses that the water of reaction and the water originating from the starting substances remain in the reaction mixture.

It is furthermore known that the distribution of isomers and homologues of the MDA can be controlled, within limits, by modifying the profiles of the dwell time and temperature. As described in EP-A-10 53 222, a high temperature is advantageous if 2,4'-MDA and 2,2'-MDA-rich types are preferably to be prepared.

It follows from the prior art, that the increasing amount of 2,4'-MDA formed at a low degree of protonation can be at least partly avoided by low temperatures during the rearrangement. A low degree of protonation, however, means a lower consumption of acid catalyst, and also a lower consumption of base required to neutralize the acid catalyst after the condensation reaction. A procedure with a low degree of protonation is, therefore, particularly economical.

However, the lower limit of the technically realizable protonation, surprisingly, is not marked by limits in the adjustment of the temperature and/or dwell time. Rather, it is found in the processes described in the prior art, that the acid reaction mixtures become heterogeneous or two-phase in the reaction below a degree of protonation of 25% (see, for example, DE-A-198 04 918). This two-phase nature leads to problems in conducting the reaction.

Therefore, an object of the present invention was to provide a simple and economical process for the preparation of polyamines of the diphenylmethane series in which the acid catalyst can be employed with degrees of protonation of <15%, without the reaction mixture demixing into a two-phase system. It is at the same time desired that polyamines having low isomer ratios of 2,4'-MDA to 4,4'-MDA be prepared.

SUMMARY OF THE INVENTION

The present invention comprises a process for the acid-catalysed preparation of polyamines of the diphenylmethane series. This process comprises
 a) reacting aniline and formaldehyde in a molar ratio of 1.5:1 to 6:1, at temperatures of 20° C. to 100° C., preferably 30° C. to 95° C., and more preferably 40° C. to 90° C., in which the water content in the acid reaction mixture is <20 wt. % and a degree of protonation of <15% is established, and
 b) increasing the temperature of the reaction mixture to 110° C. to 250° C. when the ratio of the weight contents of p-aminobenzylaniline to 4,4'-MDA in the acid reaction mixture falls below a value of 1.00.

In one embodiment of the process according to the invention, aniline is first mixed with the acid catalyst, and then formaldehyde is added. However, it is also possible to mix the aniline, formaldehyde and acid catalyst in another sequence, or also to simultaneously mix these components. Preferably, the acid catalyst is mixed with aniline and/or formaldehyde with specific power inputs of greater than 10 kW/m$^3$ of mixing volume, and more preferably greater than 20 kW/m$^3$ of mixing volume. In this context, the power input, for example, in a mixing nozzle, results from the pressure loss of the pressure pump upstream and the volume of the mixing nozzle.

The present invention relates to a process in which, in step a), aniline and formaldehyde are first reacted in the absence of the acid catalyst, to yield the aminal, and then the acid catalyst is added to the aminal and the reaction is continued at temperatures of 20° C. to 100° C. The acid reaction mixture obtained in this way has a water content of 0 to 20 wt. %, based on 100 weight % of the acid reaction mixture.

The invention relates specifically to a process, in which, in step a), after the reaction to yield the aminal, at least some of the water is first removed from the aminal, such that a water content of 0 to 5 wt. % is established in the aminal. Then, the acid catalyst is added to the aminal, and the reaction is continued at temperatures of 20° C. to 100° C. and with water contents of the acid reaction mixture obtained in this way of 0 to 20 wt. %.

DETAILED DESCRIPTION OF THE INVENTION

The process according to the present invention can be carried out both continuously and semi-continuously, as well as discontinuously. The conventional reaction apparatuses of the prior art are suitable for use herein. Suitable apparatuses include, for example, stirred reactors, tube reactors or also tube reactors with baffles, such as perforated plates, which influence the dwell time characteristics in the reactor. A combination of several reactor types is also suitable.

Polyamines of the diphenylmethane series can be prepared at degrees of protonation of <15%, preferably 4 to 14%, and more preferably 5 to 13%, with the process according to the present invention. In this context, the degree of protonation in the case of monoproton acid catalysts (such as, e.g. hydrochloric acid) is the molar ratio of the amount of acid catalyst employed and the molar amount of amine functions present in the reaction mixture.

In the case of di- and multi-proton (n-proton) acids, the degree of protonation is correspondingly the molar ratio of twice or n times the amount of acid catalyst employed and the molar amount of amine functions present in the reaction mixture.

Suitable polyamine mixtures of the diphenylmethane series are conventionally obtained by condensation of aniline and formaldehyde in a molar ratio of 1.5:1 to 6:1, and preferably 1.8:1 to 5:1.

Formaldehyde is conventionally employed industrially as an aqueous solution which is present in concentrations of 30 to 50 wt. %. However, it is also possible to employ aqueous formaldehyde solutions of another concentration or other compounds which supply methylene groups, such as e.g. polyoxymethylene glycol, para-formaldehyde or trioxane.

Acid catalysts which have proved suitable for the present invention are strong organic and, preferably, inorganic acids. Suitable acids include, for example, hydrochloric acid, sulfuric acid, phosphoric acid and methanesulfonic acid. Aqueous hydrochloric acid is preferably employed in the process according to the invention. The aqueous hydrochloric acid conventionally comprises hydrogen chloride in concentrations of 25 to 36 wt. %, based on the weight of the aqueous hydrochloride acid.

The process according to the present invention can be carried out by a procedure in which aniline, formaldehyde solution and aqueous HCl are introduced into a stirred tank and are mixed. In parallel with the reaction taking place, the majority of the water is removed by separating off by distillation, and a water content of 0 to 20 wt. %, based on 100 wt. % of the acid reaction mixture, is established. Aniline, formaldehyde solution and aqueous HCl can, optionally, also be added over time-related metering profiles in a discontinuous process, with it being possible for the removal of water to occur during or after the addition of the educts, for example, by means of vacuum distillation. The mixing of aniline, formaldehyde solution and aqueous HCl preferably takes place at temperatures of 20 to 60° C.

The invention preferably relates to a process in which aniline and formaldehyde are first reacted in the absence of the acid catalyst to give the aminal, and the acid catalyst is then added to the reaction mixture. The mixing of the aminal with the acid catalyst here preferably takes place with a specific power input of greater than 10 kW/m$^3$ of mixing volume, and more preferably with a specific power input of greater than 20 kW/m$^3$ of mixing volume, and preferably at temperatures of 20 to 60° C. The addition of the acid catalyst and the removal of the water can be carried out, for example, such that aqueous HCl is added into a stirred tank containing the resultant aminal, and the majority of the water is removed by separating off by distillation during the reaction to give the condensation product and to provide a water content of 0 to 20 wt. %, based on 100 weight % of the acid reaction mixture.

In a preferred embodiment of this process, after the reaction to yield the aminal, at least some of the water is first removed from this, such that a water content of 0 to 5 wt. %, based on the weight of the aminal, is obtained. The aminal is then mixed with acid catalyst, the mixing preferably taking place at temperatures of 20 to 60° C., and the acid reaction mixture obtained in this way is reacted at temperatures of 20° C. to 100° C. and at water contents of 0 to 20 wt. %, based on 100 weight % of the acid reaction mixture obtained, to yield the condensation product. The mixing of the aminal with the acid catalyst is preferably carried out here with a specific powder input of greater than 10 kW/m$^3$ of mixing volume, and more preferably greater than 20 kW/m$^3$ of mixing volume.

In this preferred embodiment of the process, aniline and formaldehyde are first mixed in the absence of the acid catalyst, and are reacted at temperatures of 20° C. to 100° C., preferably 40° C. to 100° C., and more preferably 60° C. to 95° C. Condensation products of aniline and formaldehyde (so-called aminal) are formed in this reaction. After the aminal formation, at least some of the water contained in the aminal is removed, for example, by phase separation or by other suitable processes such as, for example, by distillation. This results in a reaction product having a water content of 0 to 5 wt. %, preferably 0.5 to 5 wt. %, particularly preferably 1 to 4 wt. %, based on the weight of the aminal. The water content can be determined, for example, by the method of Karl-Fischer, which is described e.g. in Jander, Jahr, Maβanalyse, 15th ed., de Gruyter, Berlin (1989), p. 289 to p. 292.

The aminal is then mixed with the acid catalyst, preferably at temperatures of 20-60° C., and with specific power inputs of preferably greater than 10 kW/m$^3$ of mixing volume, and more preferably greater than 20 kW/m$^3$ of mixing volume , and the mixture is subjected to a preliminary reaction in a dwell apparatus or a sequence of dwell apparatuses at 20° C. to 100° C., and preferably 30° C. to 95° C. The water content of the resulting acid reaction mixture here is between 0 and 20 wt. %, based on 100 weight % of the acid reaction mixture. The amount of acid catalyst is chosen here such that a degree of protonation of <15%, preferably of 5 to 14%, and more preferably of 6 to 13% is established.

In step b) of the process according to the invention, the temperature of the reaction mixture is brought in stages or continuously, and optionally, under increased pressure, to a temperature of 110° C. to 250° C., preferably to 110° C. to 180° C., and more preferably to a temperature of 110° C. to 160° C. According to the invention, in this context the temperature is increased in step b) at the earliest when the ratio of the weight contents of p-aminobenzylaniline and 4,4'-MDA in the acid reaction mixture falls below a value of 1.00, preferably below a value of 0.50, more preferably below a value of 0.25, and most preferably below a value of 0.20.

The temperature in step b) is preferably kept in this temperature range for a dwell time of 20 to 300 min, more preferably 40 to 200 min, and most preferably 50 to 180 min, in order to ensure complete conversion. Adhering to these conversion/temperature limits ensures that the weight ratio of the 2,4'- and 4,4'-MDA isomers in the product is between 0.05:1.00 and 0.15:1.00.

To determine the ratio of the weight contents of p-aminobenzylaniline and 4,4'-MDA in the acid reaction mixture, the weight content of these components can be determined, for example, by analysis by means of HPLC on a reverse phase column by means of gradient elution with a solvent mixture of methanol, acetonitrile and water. Detection of the components here is preferably by a UV detector at a wavelength of 254 nm. A procedure is followed here, for example, in which the preliminary reaction is carried out at temperatures of 20 to 100° C., and samples are taken from the acid reaction mixture and these are analysed for the weight ratio of p-ABA to 4,4'-MDA. It should be ensured here that the composition of the acid reaction mixture does not change between the removal of the sample and the analysis. This can be achieved by, for example, cooling the acid reaction mixture severely, for example, to temperatures below 0° C., so that the rate of reaction becomes so low that the composition no longer changes noticeably. It is also possible to add a base to the acid reaction mixture, so that the acid catalyst is withdrawn from the reaction and this comes to a halt as a result. In a discontinuous procedure, for example, a sample can be removed from the reaction tank and analysed in any desired sequence of time, or also at regular intervals of 60 min, and preferably 30 min. When the ratio of p-ABA to 4,4'-MDA falls below a value of 1.00, the mixture can be heated up to temperatures of greater than or equal to 110° C. In a continuous procedure, in which, for example, the preliminary reaction takes place at 20 to 100° C. in at least one reaction apparatus or in a sequence of reaction apparatuses, samples can be taken, for example, at the exit of the last reaction tank and analysed in the manner mentioned above.

If the ratio of p-ABA to 4,4'-MDA exceeds the value of 1.00, the course of the reaction is to be controlled by suitable measures such that the value then falls below 1.00. For example, the throughput of acid reaction solution can be reduced such that due to the now increased dwell time, a higher conversion of the preliminary reaction is achieved at the exit of the last reaction tank and the ratio of p-ABA to 4,4'-MDA is now a value less than 1.00. However, it is also possible to adapt the temperature in the reaction tank used for the preliminary reaction or the temperature profile in the reaction tanks used for the preliminary reaction such that at the exit of the last tank the ratio of p-ABA to 4,4'-MDA is a value less than 1.00 as long as the temperature or temperature profile is kept within the limits of 20 to 100° C.

The reaction of aniline and formaldehyde in the presence of an acid catalyst to give polyamines of the diphenylmethane series can be effected in the presence of further substances, e.g. salts or organic and inorganic acids.

As a result of the process according to the invention, in spite of the low degree of protonation of <15%, no demixing occurs during the reaction. This is of course, an advantage, since at a low degree of protonation and at the same time a high water content, the acid reaction mixture dissociates into an aqueous and an organic phase, and large parts of the acid catalyst pass into the aqueous phase and are no longer available to the organic phase without limitation, and are thus, withdrawn from the reaction. This leads, on the one hand, to a lower rate of reaction, and for this reason, a longer dwell time is required for the reaction. However, this impairs the profitability of the process. On the other hand, this leads to an unfavorable product composition, since, for example, more undesirable 2,4'-MDA is then formed.

At the same time, as a result of the process according to the invention, MDA can be obtained in a weight ratio of the 2,4'-MDA to 4,4'-MDA isomers of between 0.05:1.00 and 0.15:1.00. The ratio of p-aminobenzylaniline to 4,4'-MDA is a measure of the conversion achieved. High temperatures during the reaction of the p-aminobenzylaniline and other isomeric aminobenzylanilines and those having a higher number of rings promote the formation of the 2,2'- and 2,4'-MDA isomers. This means that 2,4'-MDA is formed in large amounts if a large part of the conversion is achieved at a high temperature, i.e. above 110° C. Conversely, less 2,2'- and 2,4'-MDA, and in return more 4,4'-MDA, is formed if a large part of the conversion is achieved at lower temperatures. The formation of 4,4'-MDA can therefore be promoted, and the formation of 2,2'- and 2,4'-MDA impeded with the process according to the invention. This is due to the fact that in the process according to the invention, the temperature of the reaction mixture is only increased to 110 to 250° C. when the ratio of the parts by weight of p-aminobenzylaniline and 4,4'-MDA is a value less than 1.00. As a result, the weight ratio of the 2,4'- and 4,4'-MDA isomers in the product is between 0.5:1.00 and 0.15:1.00.

For working up the acid reaction mixture, the reaction mixture is neutralized with a base in accordance with the prior art. According to the prior art, the neutralization is conventionally carried out at temperatures of, for example, 90 to 100° C., without the addition of further substances (H. J. Twitchett, Chem. Soc. Rev. 3(2), 223 (1974)). However, it can also be carried out at another temperature level, in order to, e.g., accelerate the degradation of troublesome by-products. Suitable bases include, for example, the hydroxides of the alkali metal and alkaline earth metal elements. Aqueous NaOH is preferably used.

The base employed for the neutralization is employed in amounts of greater than 100%, preferably of 105 to 120% of the amount required stoichiometrically for the neutralization of the acid catalyst employed.

After the neutralization, the organic phase is conventionally separated from the aqueous phase in a separating tank. The product-containing organic phase remaining after the aqueous phase has been separated off is subjected to further working up steps (e.g. washing), and then freed from excess aniline and other substances present in the mixture (e.g. further solvents) by suitable processes, such as, e.g., distillation, extraction or crystallization.

The polyamine or polyamine mixture of the diphenylmethane series obtained in this way can be reacted with phosgene by known methods in an inert organic solvent to yield the corresponding di- and poly-isocyanates of the diphenylmethane series, i.e. MDI. The molar ratio of crude MDA to phosgene is expediently chosen such that 1 to 10 mol, preferably 1.3 to 4 mol of phosgene are present in the reaction mixture per mol of $NH_2$ group. Chlorinated, aromatic hydrocarbons, such as e.g. monochlorobenzene, dichlorobenzenes, trichlorobenzenes, the corresponding toluenes and xylenes as well as chloroethylbenzene, have proved to be suitable inert solvents. Monochlorobenzene, dichlorobenzene or mixtures of these chlorobenzenes are used in particular as inert organic solvents. The amount of solvent is expediently chosen such that the reaction mixture has an isocyanate content of 2 to 40 wt. %, preferably between 5 and 20 wt. %, based on the total weight of the reaction mixture. When the phosgenation has ended, the excess phosgene, the inert organic solvent or mixtures thereof, are separated off from the reaction mixture by distillation.

The products, known according to the prior art, of the polymeric MDI series containing di- and polyisocyanates of the diphenylmethane series having two or more rings, and of the monomeric MDI series containing diisocyanates of the diphenylmethane series having two rings, in particular highly viscous polymeric MDI types of 80 to 3,000 mPas at 25° C., 4,4'-MDI of technical-grade purity and/or 2,4'-MDI of technical-grade purity as well as mixed forms thereof, can be prepared from the crude MDI obtained. These products can be separated off from the crude MDI by processes according to the prior art, for example, by distillation. These products are suitable for use as raw materials for polyurethane preparation in the form of polymers and prepolymers by reaction with polyols.

The invention is to be explained in more detail with the aid of the following examples.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

For the determination of the composition of the polyamine mixture, this was separated by means of an HPLC 1050 from Hewlett Packard by reverse phase chromatography on a C18 column by means of gradient elution with a ternary mixture of methanol, acetonitrile and water using a UV detector at a wavelength of 254 nm. The components p-ABA and 4,4'-MDA were seen as clearly separated individual signals. Samples from the acid reaction mixture were neutralized before the analysis.

Example 1 (Not According to the Invention, Two-phase Reaction Mixture)

310 g of a 31.7 wt. % strength aqueous formaldehyde solution were added dropwise to 670 g aniline at 80° C. over the course of 20 min, while stirring. After the addition, the mixture was stirred at 80° C. for a further 5 min., and then cooled to 35° C. 83.0 g of a 31.9 wt. % strength aqueous hydrochloric acid were added to the reaction mixture at this temperature, while stirring intensively. The water content of the acid reaction mixture was 30.7 wt. %. Even after heating up to 110° C., the acid reaction mixture was still clearly two-phase, i.e. without the action of a stirrer, dissociation of the acid reaction mixture into an aqueous and an organic phase occured.

Example 2 (Not According to the Invention, Complete Conversion at >110° C.)

For preparation of the aminal, 334 g of a 32.1 wt. % aqueous formaldehyde solution were added dropwise to 931 g aniline at 80° C. over the course of 20 min, while stirring. After the addition, the mixture was stirred at 80° C. for a further 5 min., and a phase separation was carried out at 70 to 80° C. 900 g of the organic phase, i.e. the aminal, were mixed with 137 g of a 32.0 wt. % aqueous hydrochloric acid at 115° C. over the course of 10 min, while stirring intensively. After the addition of hydrochloric acid, the water content was 12.0 wt. %, and the ratio of p-ABA and 4,4'-MDA was 0.27. After stirring for a further 3 h at 115° C., all the aminobenzylanilines having two rings were reacted. The ratio of 2,4'- and 4,4'-MDA was 0.38. This example demonstrated the effect on the product composition when a complete conversion was achieved at a high temperature of >110° C.

Example 3 (According to the Invention, Majority of the Conversion at 20 to 100° C.)

The process as described above in Example 2 was followed to yield the aminal. 900 g aminal were mixed with 137 g of a 32.0 wt. % strength aqueous hydrochloric acid at 45° C. over the course of 10 min, while stirring intensively. After the addition of hydrochloric acid, the water content was 12.0 wt. %, and, without the action of a stirrer, the resultant reaction mixture showed no signs of demixing into an aqueous and an organic phase. After the mixture was stirred at 45° C. for 10 min, it was heated up to 80° C. and stirred at 80° C. for a further 60 min. The ratio of p-ABA/4,4'-MDA was 0.05:1.00. The mixture was then heated up to 115° C. and stirred at this temperature for a further 3 h. Aminobenzylanilines having two rings were no longer detectable, and the ratio of 2,4'- and 4,4'-MDA was 0.14:1.00.

Compared with Example 2, a clear lowering of the ratio of 2,4'- to 4,4'-MDA was seen, since a large part of the conversion was achieved at temperatures of <110° C.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the acid-catalysed preparation of polyamines of the diphenylmethane series, comprising
   a) reacting aniline and formaldehyde in a molar ratio of 1.5:1 to 6:1 at temperatures of 20° C. to 100° C., in which the water content in the acid reaction mixture is <20 wt. % and a degree of protonation of <15% is established, and
   b) increasing the temperature of the reaction to 110° C. to 250° C. when the ratio of the weight contents of p-aminobenzylaniline to 4,4'-MDA in the acid reaction mixture falls below a value of 1.00.

2. The process of claim 1, in which step a) comprises:
   (1) first reacting aniline and formaldehyde in the absence of an acid catalyst to yield the aminal,
   (2) adding an acid catalyst to the aminal and
   (3) continuing the reaction at temperatures of 20° C. to 100° C. and at water contents of 0 to 20 wt. %.

3. The process of claim 2, in which in step a), after (1) reacting aniline and formaldehyde to yield the aminal, at least some of the water is removed from the aminal such that a water content of 0 to 5 wt. % is established in the aminal, and before (2) adding an acid catalyst to the aminal, and (3) continuing the reaction at temperatures of 20° C. to 100° C. and at water contents of 0 to 20 wt. %.

4. The process o of claim 1, in which a) the reaction between aniline and formaldehyde is at a temperature of 30 to 95° C.

5. The process of claim 1, in which the degree of protonation established in step a) is 5 to 14%.

6. The process of claim 1, in which in step b) the temperature is increased to a value of 110° C. to 180° C.

7. The process of claim 1, in which in step b), the temperature is increased to a value of 110° C. to 160° C.

8. A process for the preparation of polyisocyanates of the diphenylmethane series, comprising (A) phosgenating polyamines of the diphenylmethane series, wherein said polyamines of the diphenylmethane series are prepared by the process of claim 1.

9. A process for the preparation of polyurethanes, comprising reacting polyisocyanates of the diphenylmethane series with one or more polyether polyols and/or polyester polyols to yield polyurethanes, wherein said polyisocyanates of the diphenylmethane series are prepared by the process of claim 8.

* * * * *